(12) United States Patent
Pless et al.

(10) Patent No.: US 6,597,954 B1
(45) Date of Patent: Jul. 22, 2003

(54) SYSTEM AND METHOD FOR CONTROLLING EPILEPTIC SEIZURES WITH SPATIALLY SEPARATED DETECTION AND STIMULATION ELECTRODES

(75) Inventors: Benjamin D. Pless, Atherton, CA (US); Robert E. Fischell, Dayton, MD (US); David R. Fischell, Fair Haven, NJ (US)

(73) Assignee: NeuroPace, Inc., Mountain View, CA (US)

( * ) Notice: Subject to any disclaimer, the term of this patent is extended or adjusted under 35 U.S.C. 154(b) by 174 days.

(21) Appl. No.: 09/724,805

(22) Filed: Nov. 28, 2000

Related U.S. Application Data

(63) Continuation-in-part of application No. 09/628,977, filed on Aug. 2, 2000, now Pat. No. 6,360,122, which is a continuation of application No. 09/450,303, filed on Nov. 29, 1999, now Pat. No. 6,128,538, which is a continuation of application No. 08/957,869, filed on Oct. 27, 1997, now Pat. No. 6,016,449, application No. 09/724,805, which is a continuation-in-part of application No. 09/543,264, filed on Apr. 5, 2000, and a continuation-in-part of application No. 09/373,676, filed on Aug. 13, 1999, now Pat. No. 6,230,049.

(51) Int. Cl.$^7$ ............................ A61N 1/36; A61B 5/04
(52) U.S. Cl. ...................... 607/62; 607/45; 600/544
(58) Field of Search ...................... 607/3, 5, 62, 45; 128/898, 899, 421; 600/306, 544, 545

(56) References Cited

U.S. PATENT DOCUMENTS

| 6,016,449 A | * | 1/2000 | Fischell et al. ............... 607/45 |
| 6,227,203 B1 | * | 5/2001 | Rise et al. .................. 128/898 |
| 6,230,049 B1 | * | 5/2001 | Fischell et al. ............. 600/544 |

* cited by examiner

Primary Examiner—Tu Ba Hoang

(57) ABSTRACT

A system and method for controlling epilepsy and other neurological disorders by providing electrical stimulation to a patient's brain in response to detected neurological conditions. An implantable device includes a stimulation subsystem coupled to a stimulation electrode to provide responsive electrical brain stimulation in response to an event detected via an on-board processor's analysis of data received from a detection subsystem coupled to a detection electrode located in a different portion of the patient's brain.

12 Claims, 10 Drawing Sheets

SYSTEM AND METHOD FOR CONTROLLING EPILEPTIC SEIZURES WITH SPATIALLY SEPARATED DETECTION AND STIMULATION ELECTRODES

CROSS-REFERENCES TO RELATED APPLICATIONS

This is a continuation-in-part of U.S. patent application Ser. No. 09/543,264, filed on Apr. 5, 2000; a continuation-in-part of U.S. patent application Ser. No. 09/373,676, filed on Aug. 13, 1999 and now issued as U.S. Pat. No. 6,230,049; and a continuation-in-part of U.S. patent application Ser. No. 09/628,977, filed on Aug. 2, 2000 and now issued as U.S. Pat. No. 6,360,122, which was a continuation of U.S. patent application Ser. No. 09/450,303, filed on Nov. 29, 1999 and now issued as U.S. Pat. No. 6,128,538, which was in turn a continuation of U.S. patent application Ser. No. 08/957,869, filed on Oct. 27, 1997 and now issued as U.S. Pat. No. 6,016,449.

BACKGROUND OF THE INVENTION

The invention relates to systems and methods for treating neurological disorders, and more particularly to a system and method employing an electronic device for sensing and detecting neurological dysfunction, specifically neuronal activity characteristic of epileptic seizures, in one region of a patient's brain, and applying treatment in response thereto in another region of the patient's brain.

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20–30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease. In operation, it supplies a continuous electrical pulse stream to a selected deep brain structure where an electrode has been implanted.

A typical epilepsy patient experiences episodic attacks or seizures, which are generally defined as periods of abnormal neurological activity. As is traditional in the art, such periods shall be referred to herein as "ictal" (though it should be noted that "ictal" can refer to neurological phenomena other than epileptic seizures).

Known work on detection and treatment of epilepsy via electrical stimulation has focused on a region of the brain frequently referred to as an epileptic (or epileptogenic) focus, particularly in patients suffering from partial epilepsy (the most common form of adult-onset epilepsy). In at least some partial epilepsy sufferers, it is the area where hypersynchronous activity consistently begins; it typically spreads outward, and into other regions of the brain, from there. The characteristics of an epileptic seizure onset are different from patient to patient, but are frequently consistent from seizure to seizure within a single patient. Although seizures in a partial epilepsy sufferer frequently begin in the same region of the brain, they may secondarily generalize quickly to cover a significant portion of the brain. Patients with primary generalized epilepsy may not have any specific identifiable seizure origin.

Unfortunately, continuous stimulation of deep brain structures for the treatment of epilepsy has not met with consistent success. To be effective in terminating seizures, it has traditionally been believed that epilepsy stimulation should be performed near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment at or near the focus, based on a detection of imminent seizure.

Recent research, however, indicates that the concept of a single epileptic focus does not necessarily accurately reflect the origins of partial epilepsy, at least in humans. See J. Engel, Jr., Intracerebral Recordings: Organization of the Human Epileptic Region, J. Clin. Neurophysiol. 1993; 10(1): 90–98. The human brain is a complex system, and although an anomalous signal may first be detected via known methods at a particular location or region, that does not necessarily imply that area is the true epileptogenic origin of an epileptic seizure. Nor is the region where abnormal signals are first identified necessarily the location where it is most effective to treat a seizure or its precursor. In fact, it is possible to have multiple locations in a single patient's brain that all act as epileptic foci. And in generalized seizures, abnormal EEG signals can be found throughout a patient's brain practically simultaneously.

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp, and ECoGs use internal electrodes near the surface of the brain. ECoG signals, deep-brain counterparts to EEG signals, are also detectable via electrodes implanted under the dura mater, and usually within the patient's brain. Unless the context clearly and expressly indicates otherwise, the term "EEG" shall be used generically herein to refer to both EEG and ECoG signals.

Much of the work on detection has focused on the use of time-domain analysis of EEG signals. See, e.g., J. Gotman, Automatic seizure detection: improvements and evaluation, Electroencephalogr. Clin. Neurophysiol. 1990; 76(4): 317–24. In a typical time-domain detection system, EEG signals are received by one or more implanted electrodes and then processed by a control module, which then is capable of performing an action (intervention, warning, recording, etc.) when an abnormal event is detected.

In the Gotman system, EEG waveforms are filtered and decomposed into "features" representing characteristics of interest in the waveforms. One such feature is characterized by the regular occurrence (i.e., density) of half-waves exceeding a threshold amplitude occurring in a specified frequency band between approximately 3 Hz and 20 Hz, especially in comparison to background (non-ictal) activity. When such half-waves are detected, the onset of a seizure is identified. For related approaches, see also H. Qu and J. Gotman, A seizure warning system for long term epilepsy monitoring, Neurology 1995; 45: 2250–4; and H. Qu and J. Gotman, A Patient-Specific Algorithm for the Detection of Seizure Onset in Long-Term EEG Monitoring: Possible Use as a Warning Device, IEEE Trans. Biomed. Eng. 1997; 44(2): 115–22.

A more computationally demanding approach is to transform EEG signals into the frequency domain for rigorous spectrum analysis. See, e.g., U.S. Pat. No. 5,995,868 to Dorfmeister et al., which analyzes the power spectral density of EEG signals in comparison to background characteristics. Although this approach is generally believed to achieve good results, for the most part, its computational expense renders it less than optimal for use in long-term implanted epilepsy monitor and treatment devices. With current technology, the battery life in an implantable device computationally capable of performing the Dorfmeister method would be too short for it to be feasible.

Also representing an alternative and more complex approach is U.S. Pat. No. 5,857,978 to Hively et al., in which various non-linear and statistical characteristics of EEG signals are analyzed to identify the onset of ictal activity. Once more, the calculation of statistically relevant characteristics is not believed to be feasible in an implantable device.

U.S. Pat. No. 6,016,449 to Fischell, et al., entitled "System for Treatment of Neurological Disorders," which is hereby incorporated by reference as though set forth in full herein, describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. When a seizure is detected, the Fischell system applies responsive electrical stimulation to terminate the seizure, a capability that will be discussed in further detail below.

All of these approaches provide useful information, and in some cases may provide sufficient information for accurate detection and prediction of most imminent epileptic seizures.

Accordingly, as has been previously suggested, it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499–506. It should be noted, however, that the epilepsy detection methods described above rely, at least in part, on the continuous analysis of EEG signals. To the extent responsive electrical stimulation is applied in response to a detection of epileptiform activity, artifacts of the stimulation received by the epileptiform activity detector may be significantly disruptive of the detection algorithms. A potential solution to this problem is to blank the sensing amplifiers used to receive EEG signals during and for a period after the application of electrical stimulation, but this will lead to a loss of data during the blanking period.

To recapitulate somewhat, in general, partial epilepsy is a much more complex phenomenon than traditionally thought. It is believed to be advantageous to provide therapeutic electrical stimulation in a number of brain regions involved in a patient's epilepsy, but known approaches do not do this in any meaningful way. Given the neural organization of the brain, in a given patient it may be more effective to stimulate pathways associated with epileptogenic focus, rather than the focus itself, to disrupt or block the epileptiform activity to prevent the occurrence of a clinical seizure. It is anticipated that stimulation from contralateral structures, particularly when the focus is hippocampal, may be the preferred method of treating some types of spontaneously occurring epileptiform activity. In addition, it may be particularly advantageous to apply electrical stimulation exclusively in areas distant from an epileptogenic region, as electrical stimulation of neural tissue that is especially sensitive may contribute to or initiate the hypersynchronous activity that characterizes an epileptic seizure. And furthermore, remote stimulation would serve to advantageously reduce the effects of artifacts on, the epilepsy detection methods employed.

SUMMARY OF THE INVENTION

Accordingly, a system and method according to the invention for treating a neurological disorder such as epilepsy includes an implantable electronic device capable of detecting seizure activity and its precursors, as well as providing responsive electrical stimulation to brain tissue.

The treatment methods of the present invention can be accomplished with a number of different approaches. In a typical embodiment, an implantable neurostimulator will have at least two electrodes near or in contact with brain tissue. Those electrodes may be located in close proximity to each other on a single lead, or may be on separate leads in entirely different portions of the brain. Each electrode may be dedicated to a single purpose, either detection or stimulation, or may be switchable between detection and stimulation functions.

Sensing and stimulating electrodes according to the invention are situated in different regions of the patient's brain. The regions may be physically or functionally distinct, but at least one set of sensing and stimulating electrodes should be remote from each other to facilitate the advantages and avoid the disadvantages set forth above.

Several potential regions of interest for remote sensing and stimulation have been identified. As used herein, "remote sensing and stimulation" means sensing in one area of the brain and stimulating in another area. In particular, several of these regions are described in greater detail in the Engel article referenced above, and will be further characterized in the detailed description below.

Remote sensing and stimulation according to the invention is not necessarily constrained to being an exclusive therapy; it may be advantageously performed in concert with other treatment modalities, such as responsive drug infusion, somatosensory stimulation (including audio stimulation), or vagus nerve stimulation. Remote sensing and stimulation may also, in certain circumstances, be advantageously combined with electrical stimulation at or, near the epileptogenic region, or where a seizure or its onset is first detected.

In any event, by way of the present invention, neurological signals are received by at least one electrode and analyzed by the implantable neurostimulator to identify an epileptic seizure or, preferably, its onset in advance of any clinical symptoms, or even just the increased likelihood that a seizure may occur. Responsive electrical stimulation treatment is applied elsewhere in the patient's brain.

The application of stimulation signals remote from the epileptogenic region has several advantages. First, it is believed that such therapy will tend to avoid contributing to hypersynchronous activity in the epileptogenic region. Second, detection can be carried out at (or near) the same time stimulation is being performed, as it is less likely that the detection subsystems of the implantable neurostimulator will be affected by artifacts, specifically the stimulation signals transmitted through the brain tissue. Moreover, the ability to detect the effects of electrical stimulation on remote tissue in the patient's brain may contribute to advantages in detecting, identifying and treating seizures and other neurological events with greater precision and reliability, and with longer advance notice.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
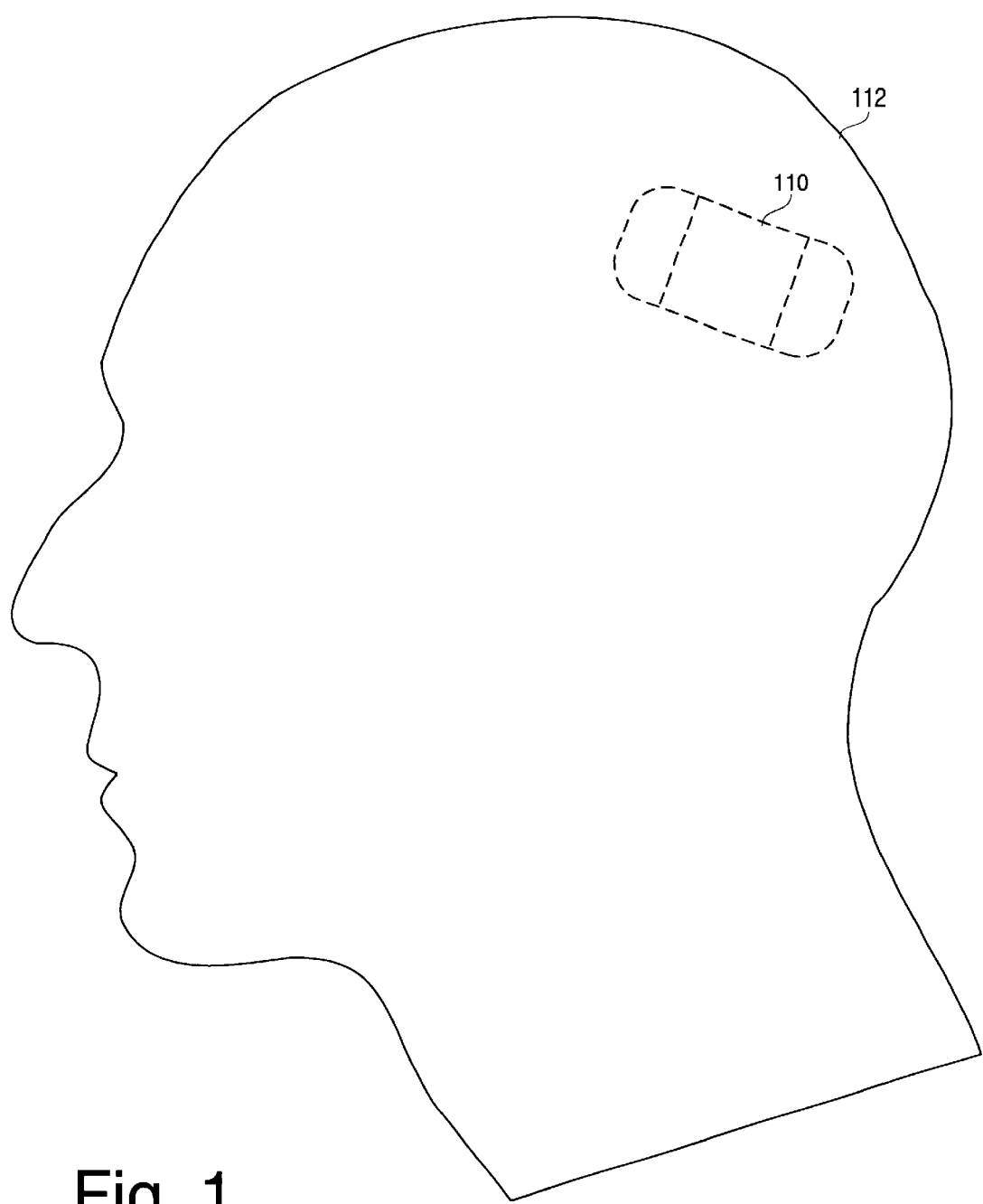
FIG. 1 is a schematic illustration of a patient's head showing the placement of an implantable neurostimulator according to an embodiment of the invention.

FIG. 1 depicts an intracranially implanted device 110 according to the invention, which in one embodiment is a small self-contained responsive neurostimulator. As the term is used herein, a responsive neurostimulator is a device capable of detecting ictal activity (or other neurological events) and providing electrical stimulation to neural tissue in response to that activity, where the electrical stimulation is specifically intended to terminate the ictal activity or treat the neurological event.

Figure 2:
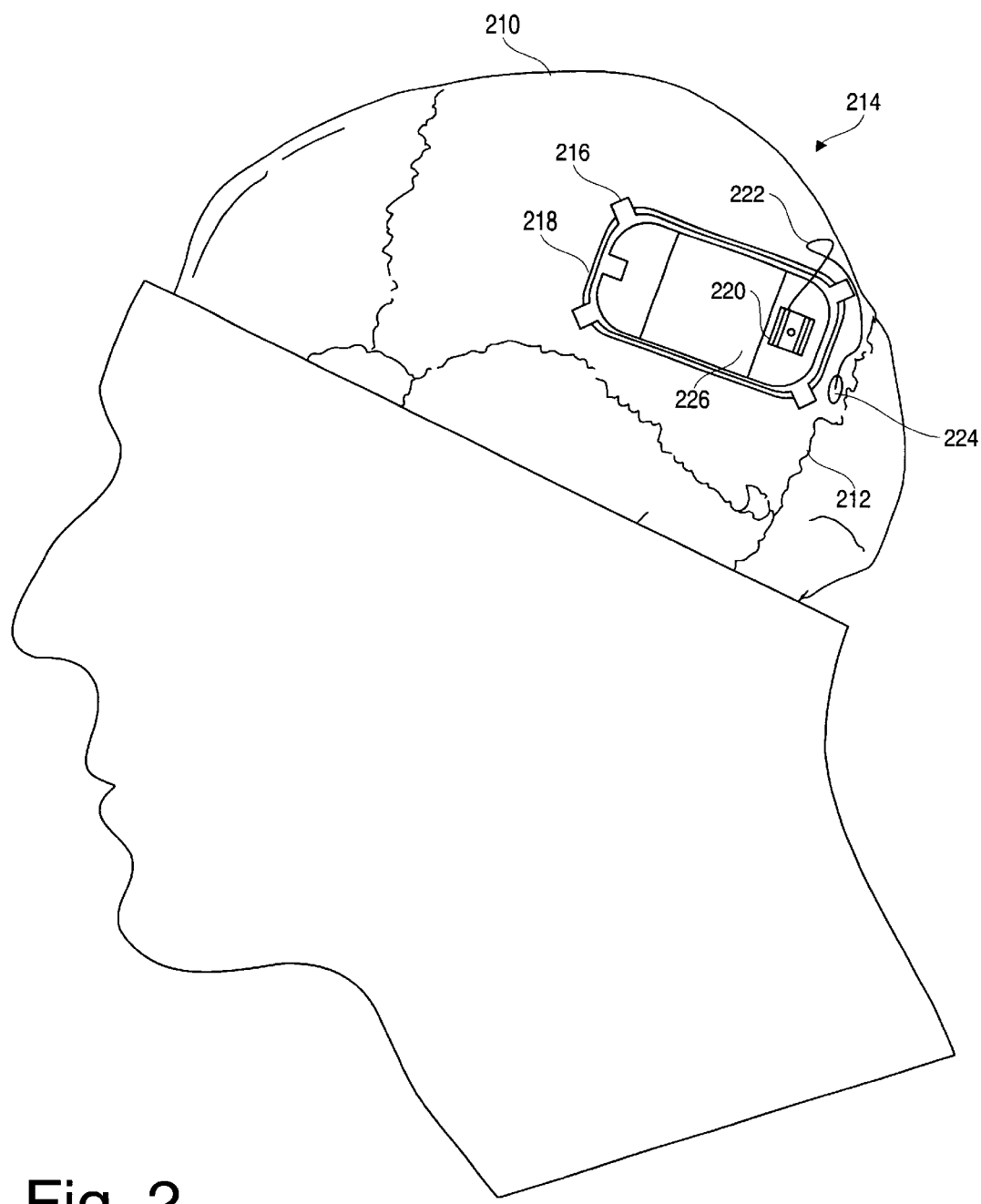
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoidal suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizure precursors (or the seizure) and preventing and/or terminating epileptic seizures. However, a primary function of a device according to the invention is to detect any increased likelihood of the brain developing a seizure by identifying trends and conditions suggesting that increased likelihood, taking actions to prevent the seizure from occurring or terminate the seizure once it has begun, and using neurological conditions (such as the characteristics of EEG signals received by the device 110) to specify or adjust the actions taken.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (see FIG. 4) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell, et al., the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
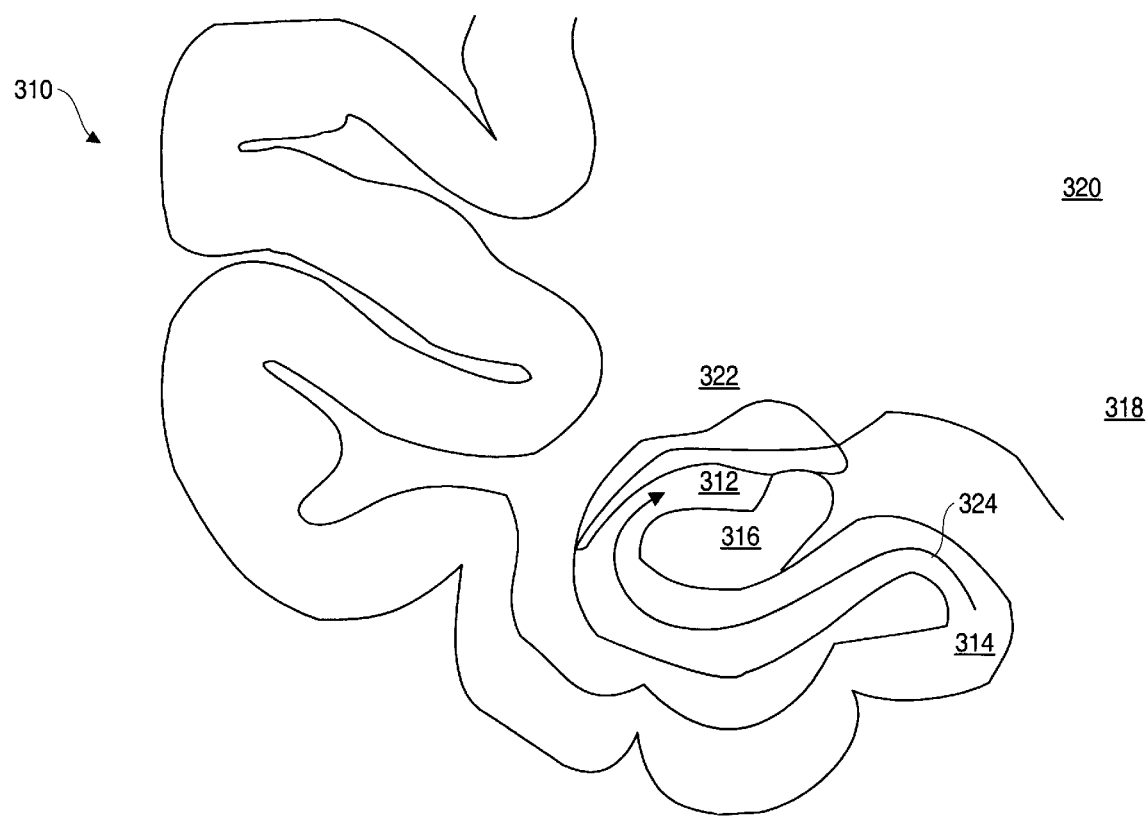
FIG. 3 is a schematic illustration of several regions in a single hemisphere of a patient's brain, including the hippocampus.

As set forth above, the invention is directed to the detection of abnormal EEG signals in one portion of a patient's brain and applying responsive therapy in a different portion of the patient's brain. An exemplary coronal section of a human brain 310, illustrating several brain anatomical details of interest, is shown in FIG. 3, which primarily shows a temporal lobe of a single hemisphere. As briefly explained above, and as described in further detail below, the limbic system is implicated in some cases of epilepsy. The normal human limbic system is responsible for processing and regulating emotions, feelings, and moods. FIG. 3 illustrates several structures of the human brain and limbic system, in particular the hippocampus 312, the parahippocampal gyrus 314, the dentate gyrus 316, the hypothalamus 318, the thalamus 320, and the amygdala 322. It is believed that some or all of these structures, as well as the functional pathways involved in communication among these structures and others, may be implicated in epilepsy. For example, see C. L. Wilson, "Neurophysiology of Epileptic Limbic Pathways in Intact Human Temporal Lobe," in P. Kotagal et al., ed., *The Epilepsies: Etiologies and Prevention*, San Diego: Academic Press 1999, 171–9, which suggests that a perforant pathway (indicated by a representative arrow 324 that is not meant to indicate the actual path of neuronal communication) between the entorhinal cortex (of which the parahippocampal gyrus 314 forms a part) and the anterior portion of the hippocampus 312 is subject to hypersynchronous neuronal activity in a substantial number of epilepsy sufferers.

The coronal brain section 310 of FIG. 3 represents a functional illustration of several structures of the limbic system. As can be appreciated, there is a complex interrelationship among the illustrated structures (in particular the hippocampus 312 and the parahippocampal gyrus 314) and many of the other structures of the limbic system; it should be noted that the gross generalization of the limbic system pathways presented herein is not a complete description of the functionality of the brain, the limbic system, or any portion thereof. It is intended to be illustrative of some diagnosis, measurement, detection, and treatment options facilitated by the invention.

Figure 4:
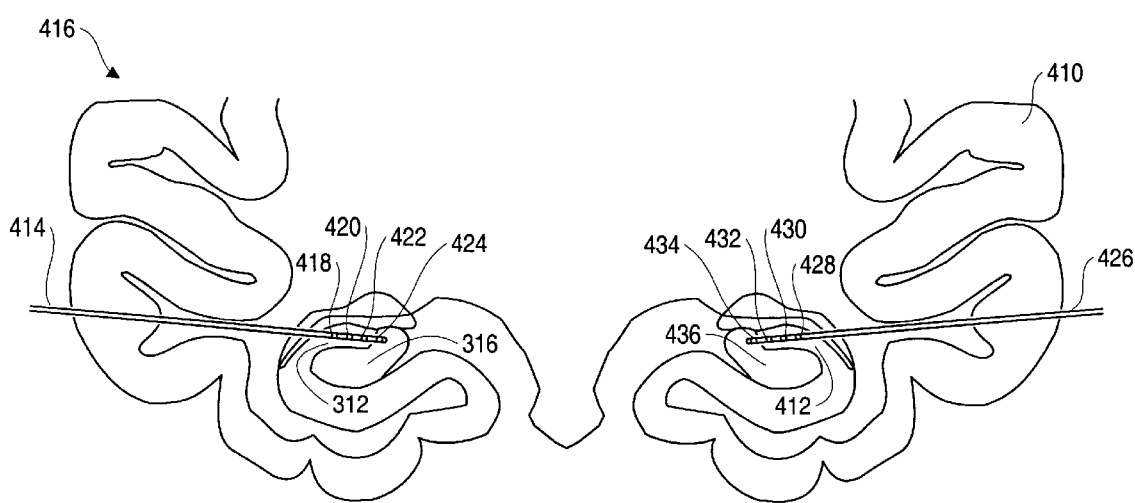
FIG. 4 is a schematic bilateral sectional view of a patient's brain, illustrating the placement of electrodes in two corresponding contralateral regions illustrated in FIG. 3 in one embodiment of the invention.

An electrode configuration capable of measuring EEG signals in a patient's hippocampus 312 and delivering electrical stimulation to a contralateral hippocampus 412 is illustrated in FIG. 4 in the context of a bilateral coronal brain section 410.

A first lead 414 is illustrated extending from outside the patient's brain 416 into the hippocampus 312. The illustrative first lead 414 has four distal electrodes 418, 420, 422, and 424. Three of the electrodes 418–422 are located in the hippocampus 312, while the most distal electrode 424 is in the dentate gyrus 316. A second lead 426 also extends from outside the patient's brain 416 and into the contralateral hippocampus 412; its four electrodes 428, 430, 432, and 434 are similarly situated in the contralateral hippocampus and contralateral dentate gyrus 436.

In one embodiment of the present invention, the first lead 414 will be used for sensing and detection, and the second lead 426 will provide responsive electrical stimulation. The individual electrodes (of the electrodes 418–424) used on the first lead 414 will be selected by the physician based on clinical judgment perhaps as a result of mapping and testing, depending at least in part on which electrodes provide effective sensing and discrimination of epileptiform activity. Likewise, the individual electrodes (of the electrodes 428–434) used for stimulation on the second lead 426 will be selected by the physician depending on which electrodes are expected to provide effective results in terminating seizure activity; some testing (as described below) may be required.

It will be appreciated that the electrode configuration illustrated in FIG. 4 is also capable of performing several alternate modes of detection and therapy. As the first lead 414 includes a plurality of distal electrodes (in the illustrated embodiment, four distal electrodes), it is possible to sense or stimulate, or both, from any one or more of those electrodes. Similarly, the second lead 426 also includes a plurality of distal electrodes, each individually selectable for sensing or stimulation. Moreover, as illustrated, both the first lead 414 and the second lead 426 extend into the patient's dentate gyri 316 and 436, respectively, so it is possible to use this electrode configuration to apply various combinations of detection and stimulation in numerous permutations of the hippocampus 312, the contralateral hippocampus 412, the dentate gyrus 316, and the contralateral dentate gyrus 436. Of course, with alternative lead configurations and approaches, numerous other combinations are also possible.

It should be noted that although electrode implantation in and around the hippocampus (and the contralateral hippocampus) is illustrated and described in some detail above, that implementation of the invention is merely illustrative, and is intended to provide an example of how the invention might advantageously be employed. In particular, as stated above, several other regions of interest for remote sensing and stimulation have been identified. Several of these regions are described in greater detail in the Engel article referenced above.

An epileptogenic lesion refers to a specific pathological cause of partial epilepsy, such as a stroke, tumor, sclerosis of brain tissue, or trauma, though the specific condition may not be readily apparent. An epileptogenic region (or ictal onset zone) is a theoretical (and difficult-to-bound) region of brain tissue necessary and sufficient to give rise to seizure activity. A focal functional deficit is an area of be brain that gives rise to abnormal non-epileptic or epileptic EEG activity. A spike focus is another term for the epileptic focus concept described above, though there is not necessarily a discrete focal generator of spike activity—EEG spikes may be distributed throughout the brain. An irritative zone is a brain region that generates interictal spikes, but is not necessary for seizure initiation (as the epileptogenic region is). As will be described in detail below, the hippocampus is particularly implicated in many cases of epilepsy, and it may be advantageous to sense or stimulate in the hippocampus (or other structures of the limbic system) regardless of the origin of abnormal EEG activity. Other locations in the temporal lobe, and elsewhere in the brain (including corresponding contralateral locations, even when seizures fail to generalize to the contralateral hemisphere), also present themselves as candidates for treatment in accordance with the invention. The possibilities are too numerous to set forth herein, but should be apparent to a neurosurgical or neurological practitioner having skill and experience in treating epilepsy.

According to Engel, the epileptogenic region, focal functional deficit, epileptogenic lesion, and spike focus need not be overlapping or even contiguous within the brain tissue. Consequently, as stated above, human partial epilepsy is a complex phenomenon, and the approach set forth herein to sense and stimulate in remote locations may provide distinct advantages over simply sensing and stimulating in the vicinity of a focus. And with regard to generalized epilepsy (either primary or secondary), there is not necessarily any single point or region of interest in the brain, and successful treatment demands an alternative approach.

Figure 5:
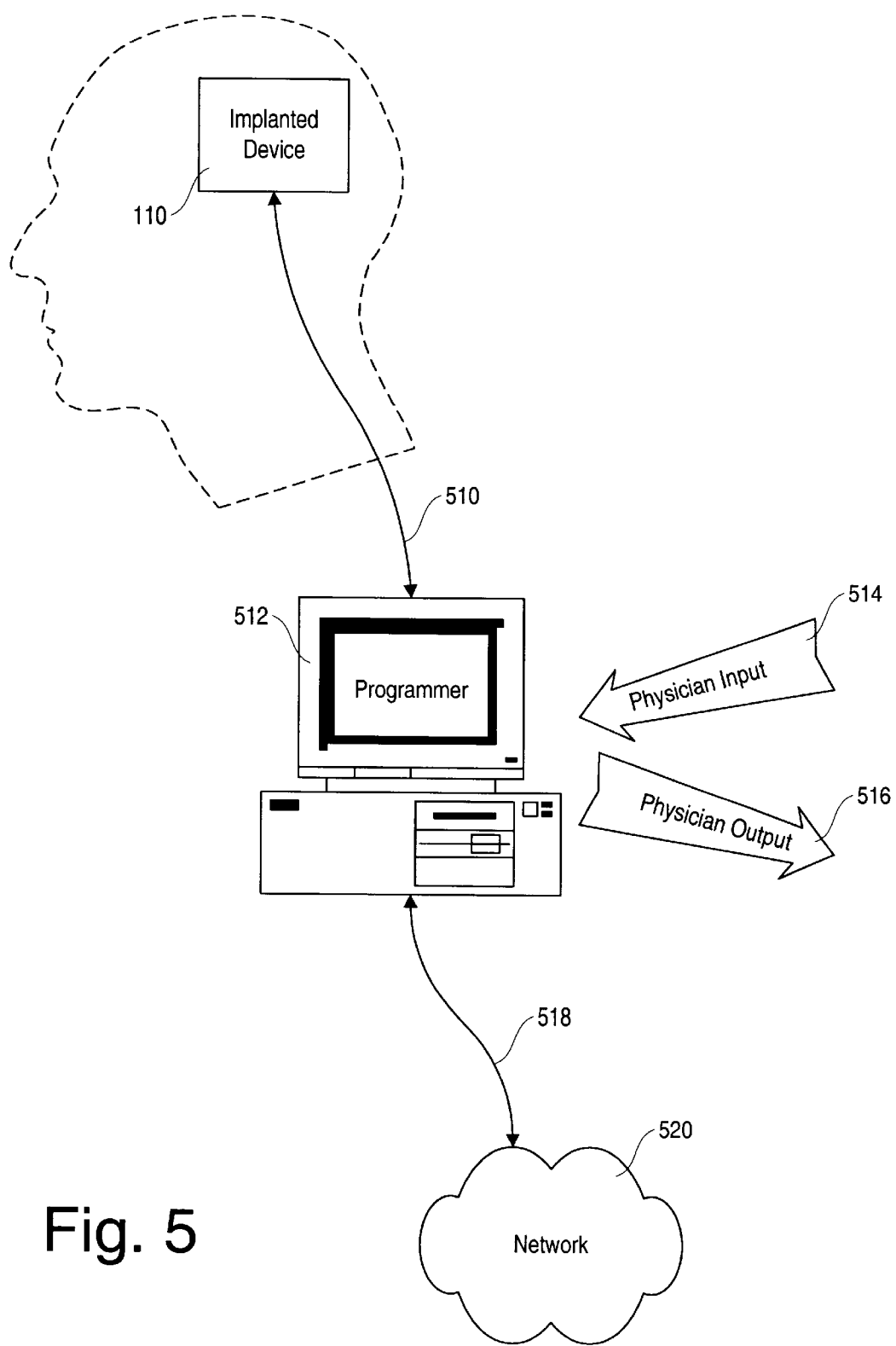
FIG. 5 is a block diagram illustrating context in which an implantable neurostimulator according to the invention is implanted and operated.

As stated above, and as illustrated in FIG. 5, a neurostimulator according to the invention operates in conjunction with external equipment. The device 110 is mostly autonomous (particularly when performing its usual sensing, detection, and stimulation capabilities), but preferably includes a selectable part-time wireless link 510 to external equipment such as a programmer 512. In the disclosed embodiment of the invention, the wireless link 510 is established by moving a wand (or other apparatus) having communication capabilities and coupled to the programmer 512 into range of the device 110. The programmer 512 can then be used to manually control the operation of the device 110, as well as to transmit information to or receive information from the device 110. Several specific capabilities and operations performed by the programmer 512 in conjunction with the device 110 will be described in further detail below.

The programmer 512 is capable of performing a number of advantageous operations in connection with the invention. In particular, the programmer 512 is able to specify and set variable parameters in the device 110 to adapt the function of the device 110 to meet the patient's needs, download or receive data (including but not limited to stored EEG waveforms, parameters, or logs of actions taken) from the device 110 to the programmer 512, upload or transmit program code and other information from the programmer 512 to the device 110, or command the device 110 to perform specific actions or change modes as desired by a physician operating the programmer 512. To facilitate these functions, the programmer 512 is adapted to receive physician input 514 and provide physician output 516; data is transmitted between the programmer 512 and the device 110 over the wireless link 510.

The programmer 512 is coupled via a communication link 518 to a network 520 such as the Internet. This allows any information downloaded from the device 110, as well as any program code or other information to be uploaded to the device 110, to be stored in a database at one or more data repository locations (which may include various servers and network-connected programmers like the programmer 512). This would allow a patient (and the patient's physician) to have access to important data, including past treatment information and software updates, essentially anywhere in the world that there is a programmer (like the programmer 512) and a network connection.

Figure 6:
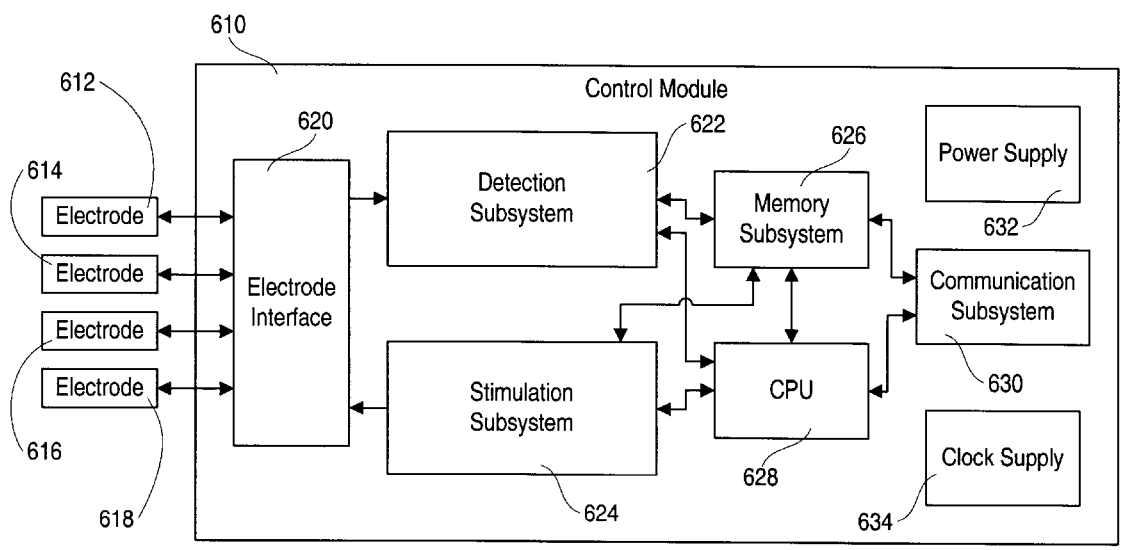
FIG. 6 is a block diagram illustrating the major subsystems of an implantable neurostimulator according to the invention.

An overall block diagram of the device 110 used for measurement, detection, and treatment according to the invention is illustrated in FIG. 6. Inside the housing 226 of the device 110 are several subsystems making up a control module 610. The control module 610 is capable of being coupled to a plurality of electrodes 612, 614, 616, and 618 (each of which may be connected to the control module 610 via a lead that is analogous or identical to the lead 222 of FIG. 2) for sensing and stimulation. In the illustrated embodiment, the coupling is accomplished through the lead connector 220 (FIG. 2). Although four electrodes are shown in FIG. 6 for simplicity of explanation, it should be recognized that any number is possible; in fact, it is possible to employ an embodiment of the invention that uses a single lead with at least two electrodes, or two leads each with a single electrode (or with a second electrode provided by a conductive exterior portion of the housing 226 in one embodiment), although bipolar sensing between two closely spaced electrodes on a lead is preferred to minimize common mode signals including noise.

The electrodes 612–618 are connected to an electrode interface 620. Preferably, the electrode interface is capable of selecting each electrode as required for sensing and/or stimulation; accordingly the electrode interface is coupled to a detection subsystem 622 and a stimulation subsystem 624. The electrode interface is also may provide any other features, capabilities, or aspects, including but not limited to amplification, isolation, and charge-balancing functions, that are required for a proper interface with neurological tissue and not provided by any other subsystem of the device 110.

The detection subsystem 622 includes an EEG analyzer function 626. The EEG analyzer function 626 is adapted to receive EEG signals from the electrodes 612–618, through the electrode interface 620, and to process those EEG signals to identify neurological activity indicative, of a seizure or a precursor to a seizure. One way to implement such EEG analysis functionality is disclosed in detail in U.S. Pat. No. 6,016,449 to Fischell et al., incorporated by reference above. The detection subsystem may optionally also contain further sensing and detection capabilities, including but not limited to parameters derived from other physiological conditions (such as electrophysiological parameters, temperature, blood pressure, etc.).

The stimulation subsystem 624 is capable of applying electrical stimulation to neurological tissue through the electrodes 612–618. This can be accomplished in any of a number of different manners. For example, it may be advantageous in some circumstances to provide stimulation in the form of a substantially continuous stream of pulses. Preferably, therapeutic stimulation is provided in response to abnormal events detected by the EEG analyzer function 626 of the detection subsystem 622. As illustrated in FIG. 6, the stimulation subsystem 624 and the EEG analyzer function 626 are connected; this facilitates the ability of stimulation subsystem 624 to provide responsive stimulation as well as an ability of the detection subsystem 622 to blank the amplifiers while stimulation is being performed to minimize stimulation artifacts. It is contemplated that the parameters of the stimulation signal (e.g., frequency, duration, waveform) provided by the stimulation subsystem 624 would be specified by other subsystems in the control module 610, as will be described in further detail below.

Also in the control module 610 is a memory subsystem 630 and a central processing unit (CPU) 632, which can take the form of a microcontroller. The memory subsystem is coupled to the detection subsystem 622 (e.g., for receiving and storing data representative of sensed EEG signals and evoked responses), the stimulation subsystem 624 (e.g., for providing stimulation waveform parameters to the stimulation subsystem), and the CPU 632, which can control the operation of the memory subsystem 630. In addition to the memory subsystem 630, the CPU 632 is also connected to the detection subsystem 622 and the stimulation subsystem 624 for direct control of those subsystems.

Also provided in the control module 610, and coupled to the memory subsystem 630 and the CPU 632, is a communication subsystem 634. The communication subsystem 634 enables communication between the device 110 (FIG. 1) and the outside world, particularly the external programmer 512 (FIG. 5). As set forth above, the disclosed embodiment of the communication subsystem 634 includes a telemetry coil (which may be situated outside of the housing 226) enabling transmission and reception of signals, to or from an external apparatus, via inductive coupling. Alternative embodiments of the communication subsystem 634 could use an antenna for an RF link or an audio transducer for an audio link.

Rounding out the subsystems in the control module 610 are a power supply 636 and a clock supply 638. The power supply 636 supplies the voltages and currents necessary for each of the other subsystems. The clock supply 638 supplies substantially all of the other subsystems with any clock and timing signals necessary for their operation.

It should be observed that while the memory subsystem 630 is illustrated in FIG. 6 as a separate functional subsystem, the other subsystems may also require various amounts of memory to perform the functions described above and others. Furthermore, while the control module 610 is preferably a single physical unit contained within a single physical enclosure, namely the housing 226 (FIG. 2), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 632 and the other functional subsystems may also vary—the functional distinctions illustrated in FIG. 6 may not reflect the integration of functions in a real-world system or method according to the invention.

Figure 7:
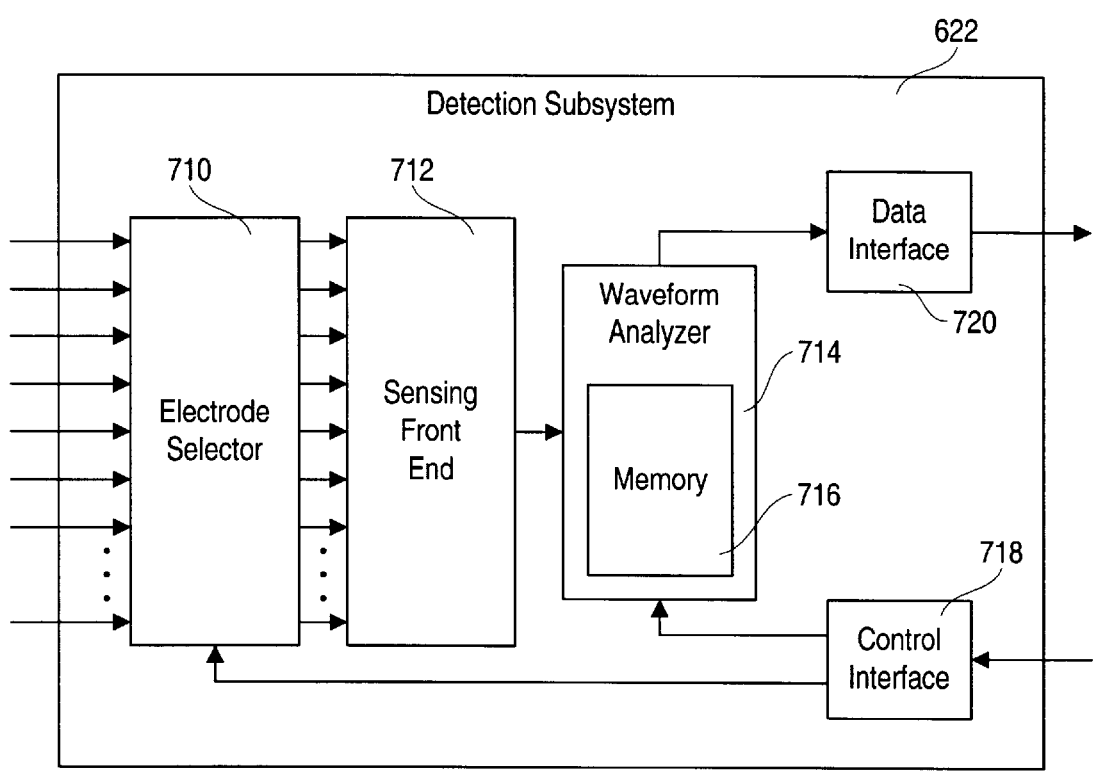
FIG. 7 is a block diagram illustrating the components of the detection subsystem of the implantable neurostimulator shown in FIG. 6.

FIG. 7 illustrates details of the detection subsystem 622 (FIG. 6). Inputs from the electrodes 612–618 are on the left, and connections to other subsystems are on the right.

Signals received from the electrodes 612–618 (as routed through the electrode interface 620) are received in an electrode selector 710. The electrode selector 710 allows the device to select which electrodes (of the electrodes 612–618) should be routed to which individual channels of the detection subsystem 622, based on control received through a control interface 718 from the memory subsystem 630 or the CPU 632 (FIG. 6). The electrode selector 710 provides signals corresponding to each selected electrode (of the electrodes 612–618) to a bank of differential amplifiers 712, which are gain-matched and adapted to amplify the input signals to a level capable of being processed by a system or method according to the invention. The bank of differential amplifiers 712 includes a plurality of channels; each channel receives a pair of electrode signals from the electrode selector 710 and amplifies the difference in potential between them to derive an analog input signal representative of the bipolar signal between two selected electrodes.

The bank of amplifiers 712 transmits the amplified analog input signals to a bank of analog-to-digital converters (ADCs) 714, which generates a number of digital signals corresponding to the analog input signals. These digital signals are passed to a multiplexer 716, which interleaves the digital signals. The multiplexed input signal is then fed from the multiplexer 716 to a signal processor 720.

Although FIG. 7 illustrates the multiplexer 716 placed between the bank of ADCs 714 and the signal processor 720, it should be noted that a multiplexing function can be performed between the electrode selector 710 and the bank of differential amplifiers 712 (which, in this embodiment, would be a single amplifier), or between the differential amplifiers 712 and the ADCs 714 (in this embodiment, a single ADC). There are tradeoffs inherent in any of these configurations that would be known to a practitioner of ordinary skill in the arts of electronics design and signal processing.

The signal processor 720 is preferably a special-purpose digital signal processor (DSP) adapted for use with the invention, or in an alternative embodiment, may comprise a programmable general-purpose DSP. In the disclosed embodiment, the signal processor has its own scratchpad memory area 722 used for local storage of data and program variables when the signal processing is being performed. In either case, the signal processor performs suitable measurement and detection methods described generally above. Any results from such methods, as well as any digitized signals intended for storage transmission to external equipment, are passed to various other subsystems of the control module 610, including the memory subsystem 630 and the CPU 632 (FIG. 6) through a data interface 724.

Figure 8:
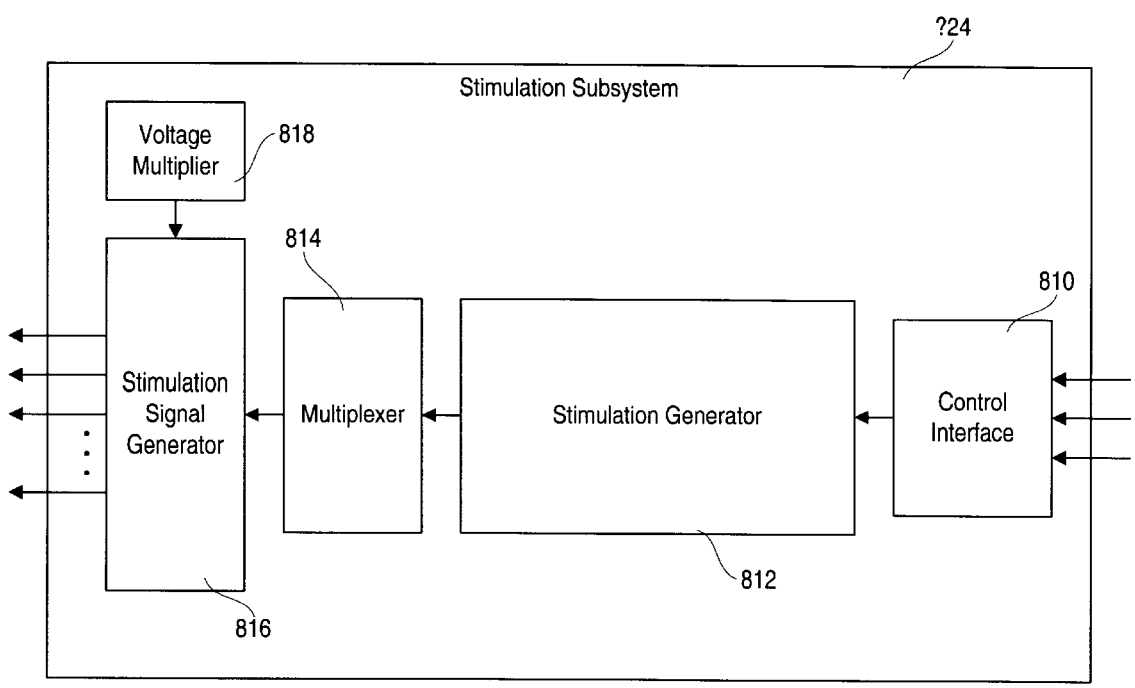
FIG. 8 is a block diagram illustrating the components of the stimulation subsystem of the implantable neurostimulator shown in FIG. 6.

The various functions and capabilities of the stimulation subsystem 624 are illustrated in greater detail in FIG. 8. Consistent with FIG. 6, inputs to the stimulation subsystem 624 are shown on the right, and outputs are on the left.

Referring initially to the input side of FIG. 6, the stimulation subsystem 624 includes a control interface 810, which receives commands, data, and other information from the CPU 632, the memory subsystem 630, and the detection subsystem 622. The control interface 810 uses the received commands, data, and other information to control a stimulation generator 812. The stimulation generator 812 is adapted to provide electrical stimulation signals appropriate for application to neurological tissue to terminate a present or predicted undesired neurological event, especially an epileptic seizure (or its precursor). As set forth above, the stimulation generator 812 is typically activated in response to conditions detected by the detection subsystem 622, but may also provide some substantially continuous stimulation.

The stimulation generator 812 is coupled to a multiplexer 814, which is controllable to select the appropriate types of stimulation and pass them along to a stimulation signal generator 816. In a presently preferred embodiment, the multiplexer 814 allows different stimulation parameters to be selectively applied to the different electrodes 612–618, either sequentially or substantially simultaneously. The stimulation signal generator 816 receives commands and data from the stimulation generator 812, and generates electrical stimulation signals having the desired characteristics that are properly time-correlated and associated with the correct electrodes, and receives power from a controllable voltage multiplier 818 to facilitate the application of a proper voltage and current to the desired neurological tissue. The voltage multiplier 818 is capable of creating relatively high voltages from a battery power source, which typically has a very low voltage; circuits to accomplish this function are well known in the art of electronics design. The stimulation signal generator 816 has a plurality of outputs, which in the disclosed embodiment are coupled to the electrode interface 620 (FIG. 6). In various embodiments of the invention, the stimulation signal generator 816 can perform signal isolation, multiplexing, and queuing functions if the electrode interface 620 does not perform such functions.

It should be recognized that while various functional blocks are illustrated in FIG. 8, not all of them might be present in an operative embodiment of the invention. Furthermore, as with the overall block diagram of FIG. 6, the functional distinctions illustrated in FIG. 8, which are presented as separate functions for clarity and understandability herein, might not be meaningful distinctions in an implementation of the invention.

For an initial detection and mapping procedure, a system according to the invention typically would be employed as follows.

Figure 9:
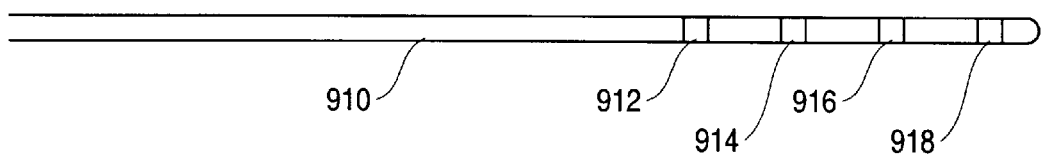
FIG. 9 is a schematic illustration of a deep brain lead having four electrodes for use in a system or method according to the invention.
Figure 10:
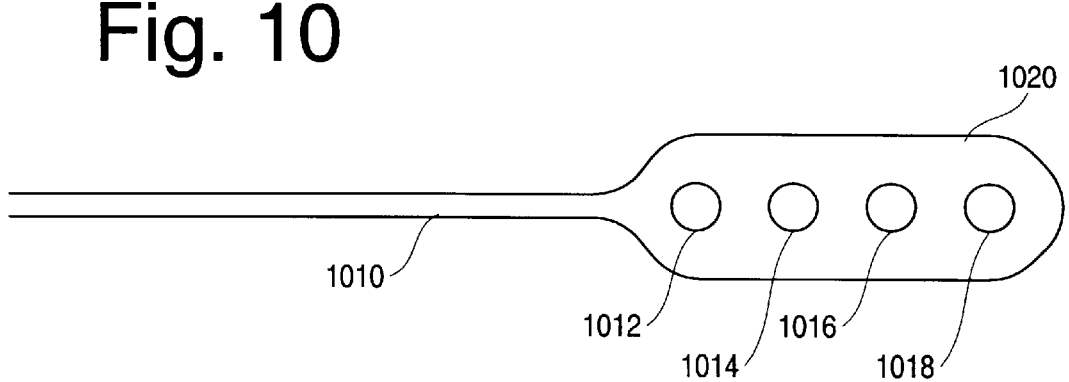
FIG. 10 is a schematic illustration of a subdural brain surface lead having four electrodes for use in a system or method according to the invention.

First, brain electrodes (including surface electrodes, depth electrodes, or a combination thereof, as described below with reference to FIGS. 9–10) are implanted by a neurosurgeon in areas believed to be relevant. As set forth above, those regions may be any of a number of structurally or functionally distinct brain areas, such as the structures of the limbic system, epileptogenic regions, focal functional deficit regions, irritative zones, focal areas, and others. EEG data would then be collected by the control module 610 of the implantable device 110 and transmitted to the programmer 512 over the wireless link 510. If it is impractical to employ the implantable device 110 for this purpose (e.g., if the necessary capabilities cannot be implemented in the required small form factor), an external apparatus having the appropriate functionality may be substituted for the implantable device 110 on a short-term (and typically inpatient) basis. After sufficient epileptiform activity has been collected by the programmer 512, a physician would use the stored EEG data, as displayed by the programmer 512, to select appropriate electrodes for sensing and stimulation by the implantable device 110. In one embodiment of the invention, the appropriate stimulation electrodes are those in the region showing the highest indication of epileptiform activity, but as set forth above in connection with the present invention, stimulation in other regions may be advantageous.

The stimulation parameters (e.g., pulse width, voltage, current, frequency, etc.) would then be selected on the programmer 512 and transmitted to the control module 610 via the wireless link 510. Various commands to start and stop stimulation on specific electrodes would also be transmitted from the programmer 512 to the control module 610.

Finally, the stimulation effects on the patient would be noted by the physician as in a standard brain mapping procedure. This standard brain mapping procedure typically uses electrodes near the site of an epileptic focus to map brain functions as a precursor to surgical excision of the epileptogenic region, but in connection with the present invention, the analogous procedure serves as an indication of where sensing and stimulation might advantageously be performed.

Thereafter, for an epileptiform activity detection and control procedure in connection with the present invention, the system would be used as follows. It will be appreciated that the programmer 512 remains in contact with the control module 610 of the implantable device 110 for much of this process.

First, brain electrodes (including surface electrodes, depth electrodes, or a combination thereof) are implanted by a neurosurgeon. EEG data is then collected by the programmer 512 from EEG signals received, amplified, and stored by the control module 610 (as described above) and transmitted to the programmer 512.

Again, after sufficient epileptiform activity has been collected by the programmer 512, a physician would use the stored EEG data, as displayed by the programmer 512, to select an appropriate set of brain electrodes for long-term sensing and stimulation by the implantable device. As illustrated in U.S. patent application Ser. No. 09/543,264 to Pless, entitled "A Neurostimulator Involving Stimulation Strategies and Process for Using It," which is hereby incorporated by reference as though set forth in full herein, the analysis performed by the physician (and automatically by the programmer 512) on the stored EEG data would be used to set parameters for epileptiform activity detection algorithms employed by,the implantable device 110 according to the invention.

Commands to start and stop electrical stimulation to the appropriate set of brain electrodes are then sent from the programmer 512 to be stored in the implantable device 110 and activated in response to a command from the physician. Stimulation is performed to induce epileptiform activity that may include after-discharges from an epileptogenic region of the patient's brain. Such after-discharges typically are similar to natural epileptiform activity. It should be noted that inducing after-discharges may require empirical testing of various stimulation parameters programmed by the programmer 512 into the implantable device 110; this procedure may require substantial physician interaction.

When induced epileptiform activity occurs, the physician uses the programmer 512 to initiate stimulation that is substantially identical to the stimulation that caused the after-discharge activity described above. If subsequent measurements through the electrodes (e.g., those on the first lead 414 of FIG. 4) show that the epileptiform activity has not terminated, the physician adjusts the stimulation parameters on the programmer 512 and causes the device 110 to re-apply stimulation until the epileptiform activity is stopped. Typically, the choice of electrodes, stimulation voltage, and/or pulse width would be adjusted until induced epileptiform activity is promptly stopped. It should be noted that if the epileptiform activity cannot be stopped, then the patient may not be a candidate for treatment via electrical stimulation, or the stimulation electrodes (e.g., the electrodes on the second lead 426 of FIG. 4) may not be appropriately placed.

It should be noted that an automated system could be used to detect natural epileptiform activity and automatically respond, thereby testing the stimulation parameters, rather than inducing artificial epileptiform activity and responding manually, as described above. If a patient experiences seizures frequently, such as every few hours, this may be a practical approach. On the other hand, if the patient has seizures infrequently, such as a small number per week, it most likely would not be practical to proceed in this manner.

After successful stimulation parameters are identified, all such parameters, including the selected stimulation electrodes, are retained in the programmer 512 and stored in the device 110. If the device 110 has not yet been implanted, or if a different apparatus is appropriate (e.g., the substitution of an implantable device for an external device used for the test procedure set forth above), the parameters are stored in the appropriate device, which is then tested for efficacy in the automatic detection and termination of seizure activity. If any adjustments are necessary, they are made by the physician, and the device 110 is implanted (along with any necessary electrodes for detection and stimulation).

For further details on the processes set forth above, see U.S. patent application Ser. No. 09/373,676 to Fischell et al., entitled "Integrated System For EEG Monitoring and Electrical Stimulation with a Multiplicity of Electrodes," which is hereby incorporated by reference as though set forth in full herein.

One significant aspect of this invention is the potential use of multiple brain electrodes to provide therapy. One embodiment of a device especially suitable for practicing certain variations of the inventive process is shown in FIG. 9. Intracerebral depth leads, which often incorporate line arrays of electrodes (as shown in FIG. 9), are useful for recording from or stimulating deep cerebral structures such as the amygdala, hippocampus, cingulate and orbital-frontal regions, which deep cerebral structures are characteristically involved in many medically refractory partial epilepsies, as described above in connection with FIG. 3. A deep brain lead 910 includes multiple distal electrodes 912, 914, 916, and 918 to enhance the ability of electrical stimulation to desynchronize brain activity to terminate epileptiform activity. Although the same burst may be delivered from a multiplicity of electrodes either in the vicinity of the epileptogenic focus or elsewhere, it is preferable to provide bursts having different parameters, particularly pulse-to-pulse timing, to achieve a greater degree of spatial heterogeneity of neural activity and thereby most effectively desynchronize brain activity. This method for terminating epileptiform activity provides additional benefits in that lower current densities at the electrodes may be used to affect a larger amount of brain tissue than if a single electrode were used. Lower current densities are associated with fewer histological changes in the vicinity of the stimulating electrodes. Furthermore, the use of different burst parameters and/or lower current densities from a number of electrodes is less likely to initiate epileptiform activity or generalize ongoing epileptiform activity.

Brain electrodes can also include electrodes placed elsewhere under the patient's scalp near or within the brain. FIG. 10 depicts a representative electrode assembly 1010 placed under the dura mater on the brain. There are four electrodes 1012, 1014, 1016, and 1018 in an insulated electrode backing 1020 that prevents current flow back to the dura mater. Current flow back to the dura matter is often uncomfortable for the patient. Although only four electrodes are illustrated in FIG. 10, it should be noted that an array of surface of electrodes usable in conjunction with the present invention and placed on the surface of the patient's brain may include more than one hundred separate electrodes.

The electrodes 1012–1018 are electrically connected to the neurostimulator (not shown) by conductors enclosed in the lead body 1022. An exemplary epileptogenic region 1024 is outlined for clarity, but is generally not visually apparent. To achieve spatial heterogeneity of electrical stimulation to most optimally desynchronize neuronal activity, the strategies described in this patent may be applied to all the electrodes 1012–1018 together or separately. It is particularly advantageous to apply separate burst parameters being applied to each of the electrodes 1012, 1014, 1016, and 1018 respectively, to desynchronize neuronal activity in a wide area of brain tissue near to or remote from the epileptogenic focus.

It should be recognized, of course, that the strategies and parameters applicable to treating an individual patient's neurological disorder may vary from case to case. For further information on the selection of advantageous parameters, see U.S. patent application Ser. No. 09/543,264, incorporated by reference above.

Figure 11:
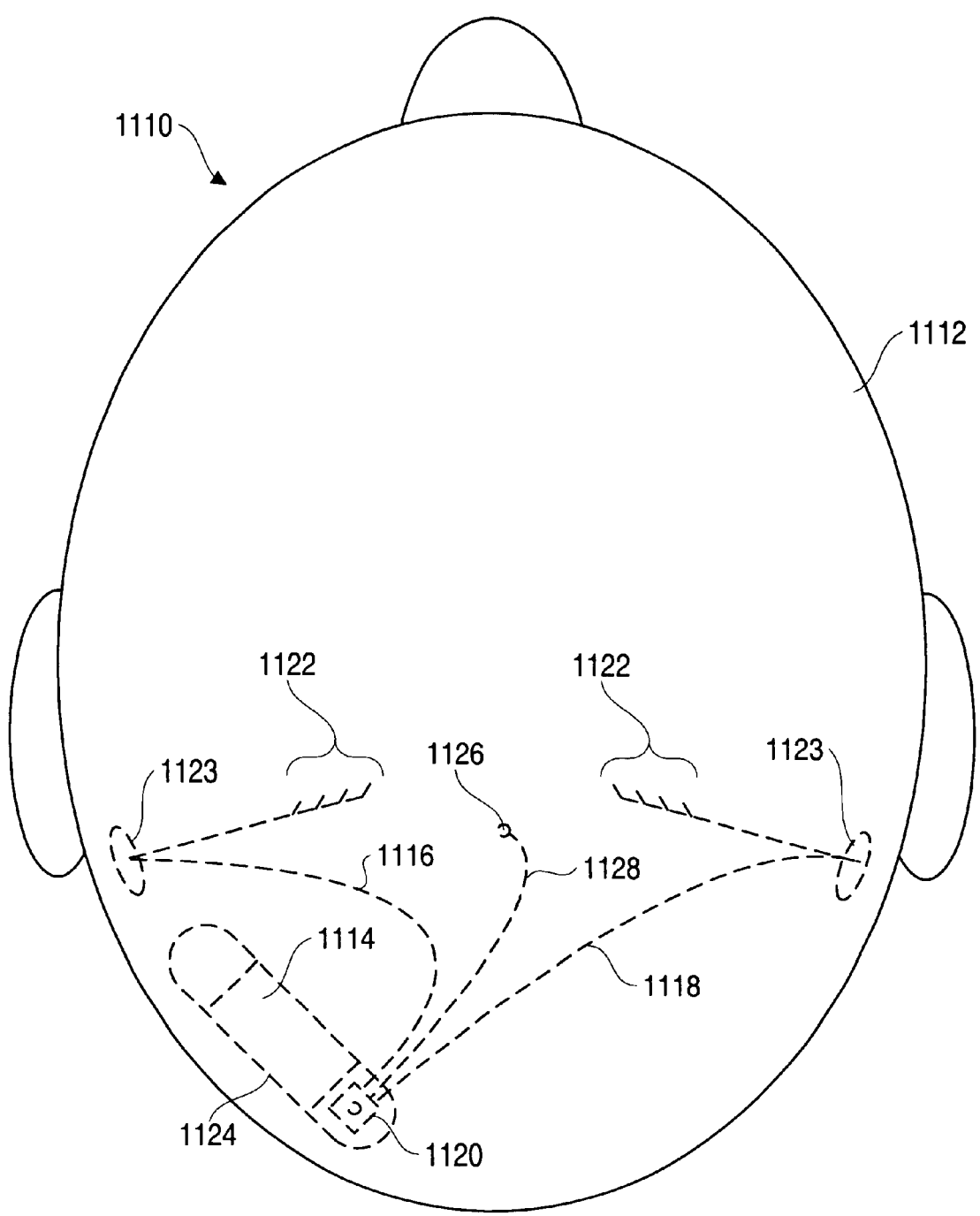
FIG. 11 is a schematic representation of a top view of a patient's head, illustrating the implantable neurostimulator connected to two deep brain leads, each with four electrodes.

FIG. 11 schematically illustrates an exemplary configuration of the implantable system 1110 for the treatment of neurological disorders as it would be generally situated under the scalp of a human head 1112 and implanted intracranially. The illustrated embodiment of the system 1110 has a control module 1114, two leads 1116 and 1118 connecting a lead connector 1120 on the control module 1114 to a plurality of distal electrodes 1122. It is envisioned that the control module 1114 is permanently implanted into the patient's cranium in a location where the bone is fairly thick. In an alternative embodiment, it is also envisioned that the control module 1114 could be located in the trunk of the patient's body like a heart pacemaker with the connecting wires being run under the patient's skin. Depending on the application, the electrodes 1122 would be placed under the cranium and above the dura mater (i.e., placed epidurally) or placed deep into the brain. The connecting leads 1116 and 1118 are run from the control module 1114, underneath the patient's scalp, through burr holes 1123 to the electrodes placed beneath the patient's cranium. Although FIG. 11 illustrates shows only four active electrodes 1122 on each of the connecting leads 1116 and 1118, it should be noted that more than four active electrodes with connecting wires may be used with and by the present invention. In the illustrated embodiment, a housing 1124 for the control module 1114, or a separate electrode 1126 (having a connecting lead 1128) could be considered a common or indifferent electrode.

As described above, the leads 1116 and 1118 carry EEG signals from the electrodes 1122 to the detection subsystem 622 (FIG. 6). The electrodes 1122 can also be energized by the stimulation subsystem 624 via the leads 1116 and 1118 to electrically stimulate the patient's brain. Although the electrodes 112 illustrated and described herein are connected to both the detection subsystem 622 and the stimulation subsystem 624 by way of the electrode interface 620, it should be apparent that a separate set of electrodes and associated wires could be used with each subsystem. Furthermore, it is envisioned that in certain circumstances, any one, several or all of the electrodes 1122 could be electrically connected (i.e., shorted) to the common electrode 1124 or 1126 or to each other. This would be accomplished by appropriate switching circuitry in the electrode interface 620 or the stimulation subsystem 624.

The general operation of the system 1110 of FIG. 11 for detecting and treating a neurological event such as an epileptic seizure would be as follows. Further information on detection methods and systems adaptable to employ the systems and methods of the current invention are set forth in detail in U.S. Pat. No. 6,016,449 to Fischell et al., incorporated by reference above.

First, the detection subsystem 622 continuously processes the EEG signals carried by the leads 1116 and 1118 from the selected electrodes 1122. When an event is detected, the detection subsystem 622 notifies the processor 628 (FIG. 6) that an event has occurred.

The processor 628 then triggers the stimulation subsystem 624 to electrically stimulate the patient's brain (or release medication, or other appropriate action) in order to stop the neurological event using any one, several or all of the electrodes 1122, as set forth above. The stimulation subsystem 624 also causes a signal to be sent to the detection subsystem 622 to disable event detection during stimulation to avoid any undesired input into the detection subsystem 622. As noted above, in an embodiment of the invention, the need for such blanking may be reduced or eliminated when the detection and stimulation sites are sufficiently separated.

The central processor 628 also preferably causes EEG signals and event-related data received from the detection subsystem 622 to be stored over a time period extending from X minutes before the event to Y minutes after the event, for storage and later analysis by the patient's physician. The value of X and Y may be set from as little as 0.1 minutes to as long as 30 minutes.

The typical stimulation signals generated by the stimulation subsystem should be biphasic (that is with equal energy positive and negative of ground) with a typical frequency of between 30 and 200 Hz, although frequencies of between 0.1 and 1000 Hz may be effective. It is also envisioned that stimulation signals having substantial DC voltage components might be used. If frequencies above 30 Hz are used, the signal generators could be capacitively coupled to the leads 1116 and 1118. The typical width of the biphasic pulse should be between 50 and 500 microseconds, although pulse widths of 10 microseconds to 10 seconds may be effective for a particular patient. Typical voltages applied may be between 10 millivolts and 20 volts rms. The stimulation would typically be turned on for several hundred milliseconds although times as short as a 1 millisecond or as long as 30 minutes may be used. Biphasic signal generation circuits are well known in the art of circuit design and need not be diagrammed here.

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect anomalous neurological characteristics in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A system for selectively initiating electrical brain stimulation to a patient's brain in response to a detected event, the system comprising:

a stimulation subsystem coupled to at least one stimulation electrode, wherein the stimulation subsystem is operative to selectively apply an electrical stimulation signal to the stimulation electrode;

a detection subsystem coupled to at least one detection electrode, wherein the detection subsystem is operative to receive and process a detected signal received by the detection electrode; and a processor operative to identify a detected event in the detected signal and to cause the stimulation subsystem to initiate application of the electrical stimulation signal in response thereto;

wherein the detection electrode is situated in a first brain region and the stimulation electrode is situated in a different second brain region.

2. The method of claim 1, wherein the system further comprises a control module, and wherein the control module includes the stimulation subsystem, the detection subsystem, and the processor.

3. The system of claim 2, wherein the detection electrode is coupled to the control module by a first lead and the stimulation electrode is coupled to the control module by a second lead.

4. The system of claim 2, wherein the detection electrode is coupled to the control module by a first lead and the stimulation electrode is coupled to the control module by the first lead.

5. The system of claim 1, wherein the first brain region comprises an epileptogenic lesion, an epileptogenic region, a spike focus, a focal functional deficit, an irritative zone, a structure of the limbic system, or a first location in the temporal lobe.

6. The system of claim 5, wherein the second brain region comprises an epileptogenic lesion, an epileptogenic region, a spike focus, a focal functional deficit, an irritative zone, a structure of the limbic system, a second location in the temporal lobe, or a contralateral location corresponding to the first brain region.

7. A method for responsively treating a neurological disorder in a patient with electrical stimulation to the patient's brain, the method comprising the steps of:

receiving a signal representative of a neurological event with a detection electrode implanted in a first region of the patient's brain;

transmitting the signal to a detection subsystem, wherein the detection subsystem is adapted to receive and process the signal received by the detection electrode;

identifying a neurological event representative of the neurological disorder with a processor coupled to the detection subsystem;

in response to the neurological event, causing a stimulation subsystem to apply an electrical stimulation signal to a stimulation electrode implanted in a second region of the patient's brain.

8. The system of claim 7, wherein the first brain region comprises an epileptogenic lesion, an epileptogenic region, a spike focus, a focal functional deficit, an irritative zone, a structure of the limbic system, or a first location in the temporal lobe.

9. The system of claim 8, wherein the second brain region comprises an epileptogenic lesion, an epileptogenic region, a spike focus, a focal functional deficit, an irritative zone, a structure of the limbic system, a second location in the temporal lobe, or a contralateral location corresponding to the first brain region.

10. A method for responsively treating a neurological disorder in a patient with electrical stimulation to the patient's brain, the method comprising the steps of:

implanting a detection electrode in a first region of the patient's brain;

implanting a stimulation electrode in a different second region of the patient's brain;

implanting a control module in the patient; and causing the control module to initiate an electrical stimulation signal to the stimulation electrode in response to an event detected in a signal received by the detection electrode.

11. The system of claim 10, wherein the first brain region comprises an epileptogenic lesion, an epileptogenic region, a spike focus, a focal functional deficit, an irritative zone, a structure of the limbic system, or a first location in the temporal lobe.

12. The system of claim 11, wherein the second brain region comprises an epileptogenic lesion, an epileptogenic region, a spike focus, a focal functional deficit, an irritative zone, a structure of the limbic system, a second location in the temporal lobe, or a contralateral location corresponding to the first brain region.

* * * * *